US005888490A

United States Patent [19]

Hall-Puzio

[11] Patent Number: 5,888,490
[45] Date of Patent: Mar. 30, 1999

[54] SHAVE GEL COMPOSITION

[75] Inventor: Patricia A. Hall-Puzio, Succasunna, N.J.

[73] Assignee: Colgate-Palmolive Company, New York, N.Y.

[21] Appl. No.: 938,511

[22] Filed: Sep. 26, 1997

[51] Int. Cl.$^6$ ........................................ A61K 7/15
[52] U.S. Cl. ................... 424/73; 424/70.19; 424/70.22; 424/70.31; 514/944
[58] Field of Search ........................ 424/73, 401, 70.19, 424/70.22, 70.31, 70.17; 514/944

[56] References Cited

U.S. PATENT DOCUMENTS 5,607,678   3/1997   Moore et al. ............................ 424/401

FOREIGN PATENT DOCUMENTS 9422415   10/1994   WIPO .

Primary Examiner—Thurman K. Page
Assistant Examiner—James M. Spear
Attorney, Agent, or Firm—Martin B. Barancik

[57] ABSTRACT

A nonaerosol shave gel composition comprising a) about 8 to about 16 wt. % of an anionic surfactant or mixture of anionic surfactant other than soap, b) about 2 to about 8 wt. % of a betaine or mixtures thereof, c) about 1 to about 4 wt. % of a foam boosting nonionic surfactant or mixture thereof d) about 1 to about 4 wt. % of an ethoxylated emollient and slip agent, e) about 0.1 to about 0.8 wt. % of a gellant comprising an ethoxylated, alkyl of 1 to 4 carbon atoms, inclusive, glycoside ester of a diacid having an alkyl group of about 8 to about 18 carbon atoms.

10 Claims, No Drawings

SHAVE GEL COMPOSITION

BACKGROUND OF THE INVENTION

Various methods of removing hair from the body have been employed for generations. Most of these methods involve a sharp tool for actual hair removal. Assisting in the removal is a chemical composition which makes hair removal easier. These compositions usually include some sort of surfactant material, emollients to make the skin feel better, slip agents for the tool to slide over the skin in an easier manner, lubricity enhancing agents to bring about a better skin feel during and after the hair removal process as well as a carrier.

Such shave assisting compositions are present in many delivery forms. They can be present as a post foaming gel, that is the gel is expressed from the container and then foams as it is rubbed into the portion of the skin from which the hair is to be removed. Other forms are merely simple shave creams or the traditional soap bar which can be lathered in a mug-shaped vehicle. With respect to the gels, they are usually expressed from the container by an aerosol delivery system. However, this is a relatively expensive form of delivery in that it requires a container which can withstand a considerable amount of pressure and also utilizes propellants which may be potentially damaging to the skin or to the environment.

Therefore, there exists a need for a non-aerosol shave gel which has the above-mentioned abilities of skin cleansing, skin conditioning, slip, and lubricity while being essentially non-irritating. Additionally, the non-aerosol nature of such a composition allows it to be packaged in a non-pressurized container. It has a further benefit of being able to be packaged in a deformable container which allows for the delivery to the skin of a predetermined, specific amount of material. Such containers can be simple squeeze tubes or any other container which can deliver the shave gel by appropriate pressure on the surface of the container or through a valve which allows the composition to be delivered through the pressure created by the hand creating a pumping action.

SUMMARY OF THE INVENTION

In accordance with the invention, there is a nonaerosol shave gel composition comprising
  a) about 8 to about 16 wt. % of an anionic surfactant or mixture of anionic surfactant other than soap,
  b) about 2 to about 8 wt. % of a betaine or mixtures thereof,
  c) about 1 to about 4 wt. % of a foam boosting nonionic surfactant or mixture thereof
  d) about 1 to about 4 wt. % of an ethoxylated emollient and slip agent,
  e) about 0.1 to about 0.8 wt. % of a gellant comprising an ethoxylated, alkyl of 1 to 4 carbon atoms, inclusive, glycoside ester of a diacid having an alkyl group of about 8 to about 18 carbon atoms.

DETAILED DESCRIPTION OF THE INVENTION

Examples of such components or anionic nonsoap surfactants are exemplified by the alkali metal salts of organic sulfate having in their molecular structure an alkyl radical containing from about 8 to about 22 carbon atoms and a sulfonic acid or sulfuric acid ester radical (included in the term alkyl is the alkyl portion of higher acyl radicals). Preferred are the sodium, ammonium, potassium or triethanolamine alkyl sulfates, especially those obtained by sulfating the higher alcohols ($C_8$–$C_{18}$ carbon atoms), sodium coconut oil fatty acid monoglyceride sulfates and sulfonates; sodium or potassium salts of sulfuric acid esters of the reaction product of 1 mole of a higher fatty alcohol (e.g., tallow or coconut oil alcohols) and 1 to 12 moles of ethylene oxide; sodium or potassium salts of alkyl phenol ethylene oxide ether sulfate with 1 to 10 units of ethylene oxide per molecule and in which the alkyl radicals contain from 8 to 12 carbon atoms, sodium alkyl glyceryl ether sulfonates; the reaction product of fatty acids having from 10 to 22 carbon atoms esterified with isethionic acid and neutralized with sodium hydroxide; water soluble salts of condensation products of fatty acids with sarcosine; and others known in the art for example taurates, phosphate, and those listed in the *McCutcheon's Encyclopedia of Surfactants*.

Preferably the anionic surfactant is an ethoxylated alkyl sulfate. Generally, the anionic surfactant is from about 8 to about 16 wt. % of the composition, preferably from about 10 to about 15 wt. % of the composition.

Examples of betaines useful herein as component b include the high alkyl betaines such as coco dimethyl carboxymethyl betaine, lauryl dimethyl carboxy-methyl betaine, lauryl dimethyl alpha-carboxyethyl betaine, cetyl dimethyl carboxymethyl betaine, lauryl bis-(2-hydroxyethyl)carboxy methyl betaine, stearyl bis-(2-hydroxypropyl) carboxymethyl betaine, oleyl dimethyl gamma-carboxypropyl betaine, lauryl bis-(2-hydroxypropyl) alpha-carboxyethyl betaine, etc. The sulfobetaines may be represented by coco dimethyl sulfopropyl betaine, stearyl dimethyl sulfopropyl betaine, amido betaines, amidosulfobetaines, and the like.

Preferably the betaine is one of lower irritation affect and mildness such as a long-chain alkyl amide alkylene betaine such as cocamidopropylbetaine.

The quantity of betaine is generally from about 2 to 8 wt. % of the composition, preferably about 4 to about 6 wt. %.

Typical examples of component c nonionic surfactants can be broadly defined as compounds produced by the condensation of alkylene oxide groups (hydrophilic in nature) with an organic hydrophobic compound, which may be alphatic or alkyl aromatic in nature. Examples of classes of nonionic surfactants are:
  1. The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 60 moles of ethylene oxide per mole of alkyl phenol. The alkyl substituent in such compounds may be derived from polymerized propylene, diisobutylene, octane, or nonane, for example.
  2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of 2,500 to 3,000, are satisfactory.
  3. The condensation product of aliphatic alcohols having from 8 to 18 carbon atoms, in either straight chain or branched chain configuration with ethylene oxide, e.g., a coconut alcohol ethylene oxide condensate having from 10 to 30 moles of ethylene oxide per mole of coconut alcohol, the coconut alcohol fraction having from 10 to 14 carbon atoms. Other ethylene oxide condensation products are ethoxylated fatty acid esters of polyhydric alcohols (e.g., Tween 20-polyoxyethylene (20) sorbitan monolaurate).

4. Long chain tertiary amine oxides corresponding to the following general formula:

$$R_1R_2R_3N \rightarrow 0$$

wherein $R_1$ contains an alkyl, alkenyl or monohydroxy alkyl radical of from about 8 to about 18 carbon atoms, from 0 to about 10 ethylene oxide moieties, and from 0 to 1 glyceryl moiety, and, $R_2$ and $R_3$ contain from 1 to about 3 carbon atoms and from 0 to about 1 hydroxy group, e.g., methyl, ethyl, propyl, hydroxy ethyl, or hydroxy propyl radicals. The arrow in the formula is a conventional representation of a semipolar bond. Examples of amine oxides suitable for use in this invention include dimethyldodecylamine oxide, oleyl-di(2-hydroxyethyl) amine oxide, dimethyloctylamine oxide, dimethyldecylamine oxide, dimethyltetradecylamine oxide, 3,6,9 trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl)amine oxide, dimethylhexadecylamine oxide.

5. Long chain tertiary phosphine oxides corresponding to the following general formula:

$$RR'R''P \rightarrow 0$$

wherein R contains an alkyl, alkenyl or monohydroxyalkyl radical ranging from 8 to 20 carbon atoms in chain length, from 0 to about 10 ethylene oxide moieties and from 0 to 1 glyceryl moiety and R' and R" are each alkyl or monohydroxyalkyl groups containing from 1 to 3 carbon atoms. The arrow in the formula is a conventional representation of a semipolar bond. Examples of suitable phosphine oxides are: dodecyldimethylphosphine oxide, tetradecylmethylethylphosphine oxide, 3,6,9-trioxaoctadecyldimethylphosphine oxide, cetyldimethylphosphine oxide, 3-dodecoxy-2-hydroxypropyldi (2-hydroxyethyl) phosphine oxide, stearyldimethylphosphine oxide, cetylethyl propylphosphine oxide, oleyldiethylphosphine oxide, dodecyldiethylphosphine oxide, tetradecyldiethylphosphine oxide, dodecyldipropylphosphine oxide, dodecyldi (hydroxymethyl)phosphine oxide, dodecyldi(2-hydroxyethyl)phosphine oxide, tetradecylmethyl-2-hydroxypropylphosphine oxide, oleyldimethylphosphine oxide, 2-hydroxydodecyldimethylphosphine oxide.

6. Long chain dialkyl sulfoxides containing one short chain alkyl or hydroxy alkyl radical of 1 to about 3 carbon atoms (usually methyl) and one long hydrophobic chain which contain alkyl, alkenyl, hydroxy alkyl, or keto alkyl radicals containing from about 8 to about 20 carbon atoms, from 0 to about 10 ethylene oxide moieties and from 0 to 1 glyceryl moiety. Examples include: octadecyl methyl sulfoxide, 2-ketotridecyl methyl sulfoxide, 3,6,9-trioxaoctadecyl 2-hydroxyethyl sulfoxide, dodecyl methyl sulfoxide, oleyl 3-hydroxypropyl sulfoxide, tetradecyl methyl sulfoxide, 3 methoxytridecylmethyl sulfoxide, 3-hydroxytridecyl methyl sulfoxide, 3-hydroxy-4-dodecoxybutyl methyl sulfoxide.

Generally, not only do these nonionic materials have surfactant activity but they are foam boosters and preferably have thickening capabilities as well. The N-oxides seem to satisfy these characteristics and are preferred as well as the long alkyl chain amides, particularly when the nitrogen of the amide bears hydroxy alkyl group(s). Even more preferably, the nonionic surfactant is a mixture of the long-chain N-oxides, particularly those N-oxides where the nitrogen bears hydroxy ethyl group(s) and the long alkyl chain amides, particularly where the nitrogen bears at least one hydroxy alkyl, preferably ethyl. Examples of such N-oxides are particularly dihydroxyethyl cocoamine oxides and other 12 to 18 carbon atom alkyl groups in the long-chain or long-chain mono hydroxyethyl N-oxide as well as lauramide dihydroxyethyl and other long-chain alkyl amides.

The quantity of nonionic surfactant(s) or preferably the above identified mixtures thereof are from about 1 to about 4 wt. % of the composition, preferably about 1.5 to 3 wt. % of the composition.

Also present in the composition is component d, an ethoxylated emollient and slip agent. Various emollients can be used, for example esters and waxes. The preferred emollient in this case is a lanolin with about 40 to about 100 ethoxy groupings. Not only do these agents provide emolliency and slip but they, particularly the lanolin based, also enhance or maintain the clarity of the composition. Particularly preferred is PEG-75 lanolin. Generally, this component is about 1 to about 4 wt. % of the composition, preferably about 1.5 to about 3 wt. %.

Component e of the composition is the gellant comprising an ethoxylated, alkyl of 1 to 4 carbon atoms substituted glycoside ester of a diacid having an alkyl group of about 8 to about 18 carbon atoms. With respect to the alkyl sugar ester of a long-chain acid, preferably the alkyl group is methyl, the sugar is glucose and the acid is dioleic. It is most preferable that the composition also be ethoxylated so as to present the appropriate dispersion and skin feel within the composition. Generally from about 50 to about 200 ethoxy groups are present, preferably 75 to about 150. The most preferable compound is PEG-120 methyl glycoside dioleate. These materials are present from about 0.1 to about 0.8 wt. % of the composition, preferably about 0.2 to about 0.5 wt. %.

Other materials may be present in the composition. Of particular interest are other emollients which can provide skin feel, slip and lubricity. Of particular interest are the polyethylene glycol of moderate molecular weight, for example about 200 to about 2,000, preferably about 400 to about 1000. PEG-12 has a molecular weight of about 600. These materials provide excellent skin feel as well as making the foam creamier as well. They can be present in the composition in quantities of about 0.2 to about 2.0 wt. %.

Humectants can also be present in the composition. Such humectants are generally polyhydric alcohols, for example glycerine, propylene glycol sorbitol and the like. Generally an excess should be avoided so as to avoid foam depression. The pH of the composition is about 6 to about 8, preferably about 6.5 to about 7.5. The viscosity of the composition is from about 25,000 to about 80,000 cps, as measured on a Brookfield RVF viscometer Ser. No. 82842, at 25° C. using T-bar A at 2 rpm.

Preservative, antioxidants, UV stabilizers, fragrances, colorants, and the like can be present as long as they are compatible with the gel and preferably maintain the clarity as well.

Below is an example of the invention. The example is intended to illustrate the invention but not reduce the broad inventive concept therein.

EXAMPLE 1

| Component | wt. % |
| --- | --- |
| Sodium laureth sulfate (2 ethoxy) | 12 |
| Cocoamidopropybetaine | 5 |
| Dihydroxyethylcocoamine Oxide | 1 |
| Lauramide diethanolamine | 0.75 |
| PEG-120 methylglycoside dioleate | 0.25 |
| PEG-75 lanolin | 1.5 |
| Preservatives | Trace |
| Water | Balance |

This composition can be readily filled with a deformable tube and the contents squeezed onto the hand for application to the portion of the body from which hair is to be removed by a sharp object such as a razor.

What is claimed is:

1. A nonaerosol shave gel composition comprising
   a) about 8 to about 16 wt. % of an anionic surfactant or mixture of anionic surfactant other than soap,
   b) about 2 to about 8 wt. % of a betaine or mixtures thereof,
   c) about 1 to about 4 wt. % of a foam boosting nonionic surfactant or mixture thereof
   d) about 1 to about 4 wt. % of an ethoxylated emollient and slip agent,
   e) about 0.1 to about 0.8 wt. % of a gellant comprising an ethoxylated, alkyl of 1 to 4 carbon atoms, glycoside ester of a diacid having an alkyl group of about 8 to about 18 carbon atoms.

2. The composition in accordance with claim 1 which is clear.

3. The composition in accordance with claim 1 wherein a is about 10 to 15 wt. %.

4. The composition in accordance with claim 3 wherein a is a laureth sulfate with an average of 2 to 3 ethoxy groups.

5. The composition in accordance with claim 1 wherein b is cocoamidopropylbetaine.

6. The composition in accordance with claim 5 wherein the betaine is present in quantities of about 4 to about 6 wt. %.

7. The composition in accordance with claim 1 wherein the nonionic surfactant is a mixture of an amine oxide and an amide.

8. The composition in accordance with claim 1 wherein d is a lanolin.

9. The composition in accordance with claim 8 wherein the lanolin has about 40 to about 100 ethoxy groups.

10. The composition in accordance with claim 1 wherein e is an ethoxylated methyl glycoside ester of dioleic acid.

* * * * *